United States Patent
Oberleitner et al.

(10) Patent No.: US 11,079,346 B2
(45) Date of Patent: Aug. 3, 2021

(54) ARRANGEMENT FOR DETERMINING THE MOISTURE OF AN OBJECT

(71) Applicant: AIT AUSTRIAN INSTITUTE OF TECHNOLOGY GMBH, Vienna (AT)

(72) Inventors: Andreas Oberleitner, Zillingdorf (AT); Robert Lurf, Gloggnitz (AT)

(73) Assignee: AIT Austrian Institute of Technology GmbH, Vienna (AT)

(*) Notice: Subject to any disclaimer, the term of this patent is extended or adjusted under 35 U.S.C. 154(b) by 184 days.

(21) Appl. No.: 15/556,421

(22) PCT Filed: Mar. 17, 2016

(86) PCT No.: PCT/AT2016/050066
§ 371 (c)(1),
(2) Date: Oct. 12, 2017

(87) PCT Pub. No.: WO2016/149720
PCT Pub. Date: Sep. 29, 2016

(65) Prior Publication Data
US 2018/0106747 A1    Apr. 19, 2018

(30) Foreign Application Priority Data
Mar. 20, 2015    (AT) .............................. A 50226/2015

(51) Int. Cl.
*G01N 27/22*    (2006.01)
*G01N 33/483*    (2006.01)

(52) U.S. Cl.
CPC ....... *G01N 27/223* (2013.01); *G01N 33/4833* (2013.01)

(58) Field of Classification Search
CPC .............. G01N 27/223; G01N 33/4833; A61B 2562/029
(Continued)

(56) References Cited

U.S. PATENT DOCUMENTS 6,249,130 B1 * 6/2001 Greer ................... G01D 5/2405
                                                          324/664
9,222,906 B2 * 12/2015 Youssi ................. G01N 27/223
(Continued)

FOREIGN PATENT DOCUMENTS

EP        2500094 A1    9/2012
WO    2012140310 A1    10/2012

OTHER PUBLICATIONS

Unander, T., et al: "Characterization of Printed Moisture Sensors in Packaging Surveillance Applications", IEEE Sensors Journal, IEEE Service Center, New York, NY, US, vol. 8, No. 8, Jun. 26, 2009 (Jun. 26, 2009).
(Continued)

*Primary Examiner* — Jeff W Natalini
(74) *Attorney, Agent, or Firm* — Laurence A. Greenberg; Werner H. Stemer; Ralph E. Locher

(57) ABSTRACT

An arrangement for determining the moisture of an object, in particular the moisture of human skin, has an electrically insulating carrier layer onto which the following units are applied: at least two electrodes, in particular interdigital electrodes, which are arranged on a first face of the carrier layer; a digital capacitance measuring device, to which the electrodes are connected; an NFC transponder which comprises an antenna and to which the measurement results of the capacitance measuring device are supplied in order to be forwarded wirelessly via the antenna, wherein the NFC transponder and the capacitance measuring device are arranged in the same chip in particular; and a shielding, which lies on the carrier layer face opposite the first face and which is connected to system ground of the capacitance measuring device in particular.

19 Claims, 6 Drawing Sheets

(58) Field of Classification Search
USPC .................................................. 324/658–690
See application file for complete search history.

(56) References Cited

U.S. PATENT DOCUMENTS

| | | | | |
|---|---|---|---|---|
| 9,880,119 | B2* | 1/2018 | Morosow | G01N 27/223 |
| 2005/0057883 | A1* | 3/2005 | Bolken | H01L 21/4803 |
| | | | | 361/301.3 |
| 2006/0186901 | A1* | 8/2006 | Itakura | G01N 27/223 |
| | | | | 324/689 |
| 2006/0272397 | A1* | 12/2006 | Hawk | B32B 17/10036 |
| | | | | 73/73 |
| 2012/0234079 | A1* | 9/2012 | Humbert | G01N 27/414 |
| | | | | 73/29.05 |
| 2013/0287062 | A1* | 10/2013 | Mayer | H01L 27/04 |
| | | | | 374/142 |
| 2013/0305822 | A1* | 11/2013 | Graf | G01N 25/56 |
| | | | | 73/431 |
| 2015/0047430 | A1* | 2/2015 | Benzel | H01L 28/60 |
| | | | | 73/335.04 |
| 2015/0048986 | A1* | 2/2015 | Huang | H01Q 7/06 |
| | | | | 343/788 |
| 2016/0025665 | A1* | 1/2016 | Hebert | G01N 27/223 |
| | | | | 324/664 |

OTHER PUBLICATIONS

Fangming, Deng, et al.: "A CMOS Humidity Sensor for Passive RFID Sensing Applications", Sensors, vol. 14, No. 5, May 16, 2014.
Rose Daniel P, et al.: "Adhesive RFID Sensor Patch for Monitoring of Sweat Electrolytes", IEEE Transactions on Biomedical Engineering, IEEE Service Center, Piscataway, NJ, USA, Nov. 11, 2014.
GoSense TH-Stat ID (TM) NFC Temp & Humidity Sensor. May 1, 2013 (May 1, 2013). pp. 1-1. XP055228577;Retrieved from the Internet: URL: http: www.gosense-wireless.comjGoSens e TH-Stat ID DS Rev1.pdf.
Wang, David: "FDC1004: Basics of Capacitive Sensing and Applications". Application Report, Dec. 1, 2014 (Dec. 1, 2014). pp. 1-12. XP055279836.

* cited by examiner

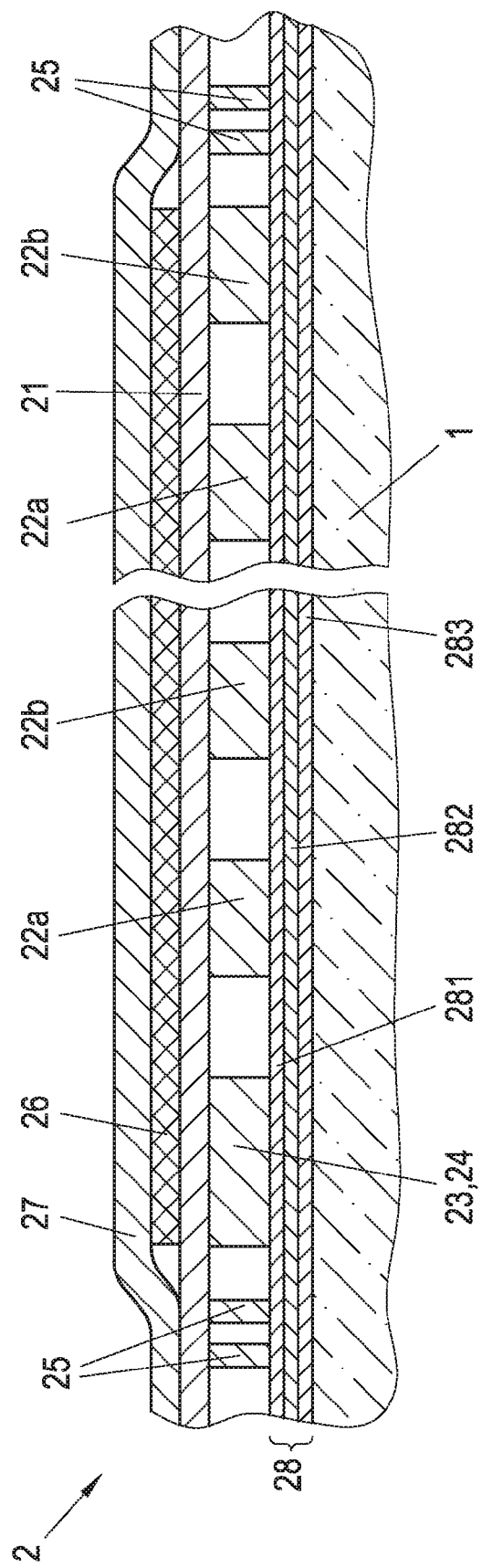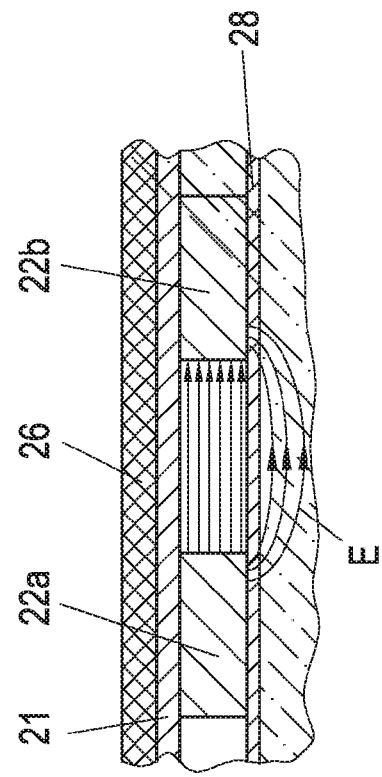

ARRANGEMENT FOR DETERMINING THE MOISTURE OF AN OBJECT

BACKGROUND OF THE INVENTION

Field of the Invention

The invention relates to an arrangement for determining the moisture of an object, in particular the moisture of human skin.

A large number of skin moisture measuring apparatuses are known from the prior art, and they all have certain disadvantages. In particular, it is difficult, in the case of such moisture measuring apparatuses, to obtain easily, in a non-contact mode, uncorrupted measurement values in each case from the same location of the skin. Moreover, in the case of tabletop apparatuses known from the prior art, although it is possible to carry out measurements under laboratory conditions, these apparatuses are not mobile. In the case of impedance methods, galvanic skin contact and hence a voltage supply are required. The data determined are not digitally available or processable further in a mobile manner.

BRIEF SUMMARY OF THE INVENTION

It is an object of the invention to solve these problems.

The invention achieves this object by means of an arrangement having the features as claimed.

The invention relates to an arrangement for determining the moisture of an object, in particular the moisture of human skin, comprising an electrically insulating carrier layer, on which the following units are applied:
  at least two electrodes, in particular interdigital electrodes, which are arranged on a first side of the carrier layer,
  a digital capacitance measuring device, to which the electrodes are connected,
  an NFC transponder having an antenna, to which NFC transponder the measurement results of the capacitance measuring device are fed for forwarding by means of radio via the antenna, wherein the NFC transponder and the capacitance measuring device are arranged in particular in the same chip, and
  a shield, which lies on the side of the carrier layer opposite the first side and is connected in particular to the system ground of the capacitance measuring device.

Such an arrangement additionally has the advantage that it is suitable for mainstream use and is producible in a favorable way and also enables a simple application with regard to reading out the object or skin moisture measurement values determined. Furthermore, on account of the non-contact manner in which the measurement is initiated, the measurement values exhibit only little dependence on contact pressure. This is important especially in the case of compressible objects such as skin, for example. This results in little influencing of the measurement value, since the measurement is carried out in a non-contact manner overall at the request of an external data communication apparatus.

In order to determine a positionally fixed measurement in particular in each case at the same location of the human body and to be able to perform a large number of multiple measurements in each case at the same location, provision can be made for
an insulation layer to be provided, which is arranged on that side of the carrier layer which is opposite the shield and bears on the electrodes, wherein in particular the insulation layer is embodied in an adhesive fashion on the side facing away from the electrodes.

An embodiment of the invention that can be manufactured easily can be achieved by virtue of the fact that the insulation layer comprises a film, on whose side facing the electrodes a first connection layer, in particular adhesive layer, is arranged, which connects the film, in particular adhesively, to the electrodes and/or the carrier layer, and a second adhesive layer for adhering to the object is present on the other side of the film facing away from the electrodes.

In order to reduce the influence of the carrier layer and adhesive layer on the measurement and to achieve a greater influence of the actual measurement variable, namely the (skin) moisture, on the measured capacitance and to reduce parasitic effects, provision can be made for the carrier layer and/or the insulation layer to have a relative permittivity of less than 20, in particular of less than 5.

In order to prevent manual access to the shield and/or the electronic components and to protect the electronic components from moisture and mechanical influences, provision can be made for a covering layer to be arranged on the side of the carrier layer on which the shield is situated.

In order to reduce the influencing by external fields and to improve the shield, provision can be made for the covering layer to be embodied in an electrically insulating fashion and for the shield to be electrically insulated from accesses from outside.

A particularly simple production of the antenna by means of printed circuits can be achieved by virtue of the turns of the antenna being applied and arranged as a conductive layer on a side of the carrier layer.

In order to achieve an adaptation of the arrangement to non-planar surfaces, such as are typical on human skin, provision can be made for the carrier layer and/or the insulation layer and/or the covering layer to have a flexible construction.

In order to achieve a recording of data values without interaction of the user and to read out said data values in a time-shifted manner, it can be provided that a battery is present, which is connected to the capacitance measuring device, and in particular
  the capacitance measuring device measures the capacitance between the electrodes at predefined points in time and stores said capacitance in a data buffer memory, wherein the NFC transponder transmits all capacitance measurement values situated in the data buffer memory upon request.

Alternatively, it is also possible for the NFC transponder to supply the capacitance measuring device with energy stored in an energy buffer store, which energy was drawn from the electromagnetic field surrounding the antenna.

In order to reduce the influence of mechanical loadings on the measurement result, provision can be made for an edge that is free of electrodes to be provided on the carrier layer, in particular on all sides, wherein the width of the edge of the carrier layer is in this case at least 15%, in particular at least 30%, of the longest dimension of the area region occupied by the electrodes.

In order to reduce the influence of mechanical loadings on the measurement result, provision can also be made for a load relieving element to be provided on that side of the carrier layer which is opposite the electrodes, said load relieving element projecting from the carrier layer and being arranged within an edge region around the electrodes which has a width greater than 15% of the longest dimension of the area region encompassed by the electrodes.

A mechanically simple and stable construction that further reduces the influence of mechanical loadings on the measurement result provides for the load relieving element to have a thickness of between 0.5 mm and 2 mm.

BRIEF DESCRIPTION OF THE SEVERAL VIEWS OF THE DRAWING

Preferred embodiments of the invention are discussed in greater detail with reference to the figures of the drawings illustrated below.

FIG. 1 shows in section an arrangement in accordance with a first embodiment of the invention.

FIG. 2 shows in detail the electrical relationships between two electrodes that are applied to human skin.

DESCRIPTION OF THE INVENTION

Figure 3:
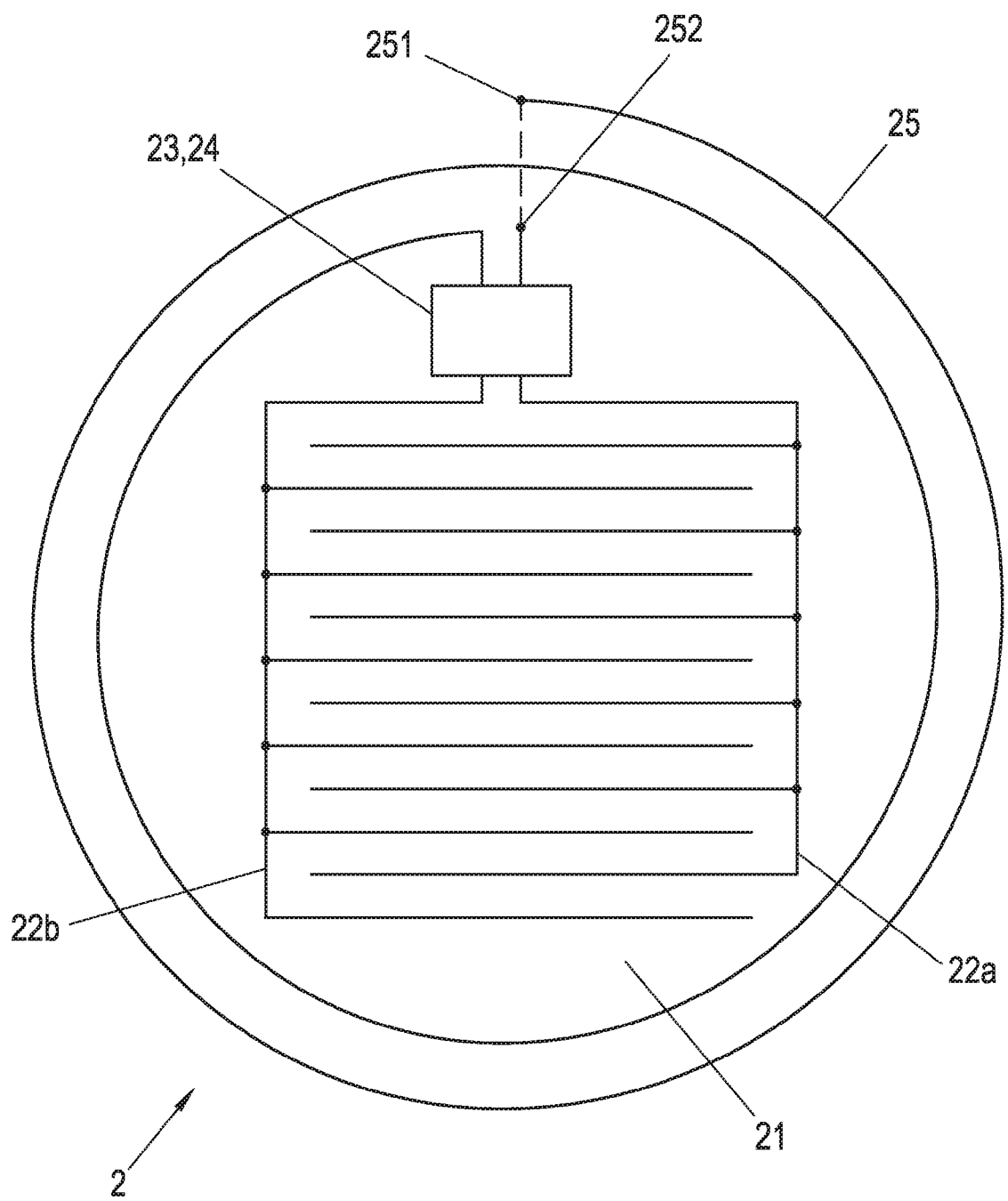
FIG. 3 shows the arrangement illustrated in FIG. 1 as viewed from the object to be examined.

The arrangement 2 for determining the moisture of an object 1 as illustrated in FIG. 1 comprises an electrically insulating carrier layer 21. Two electrodes 22a, 22b are situated on one side of the electrically insulating carrier layer 21, which electrodes as illustrated in FIG. 3, are embodied as interdigital electrodes. Furthermore, FIG. 1 illustrates a digital capacitance measuring device 23, to which the electrodes 22a, 22b are connected (FIG. 3). An NFC transponder 24 is also arranged in the same chip as the capacitance measuring device 23, said NFC transponder being connected to an antenna 25 arranged in the peripheral region of the arrangement 2. The capacitance measuring device 23 and the NFC transponder 24 can also be arranged in separate chips.

The measurement results of the capacitance measuring device 23 are fed to the NFC transponder 24. If a request from an external data communication apparatus passes via the antenna 25 to the NFC transponder 24, then the latter triggers the capacitance measuring device 23 for the measurement of the capacitance at its input, that is to say between the electrodes 22a, 22b connected to it. The capacitance measuring device 23 measures the capacitance predefined between the electrodes 22a, 22b and forwards the measurement result to the NFC transponder 24, which communicates the measurement result to the external data communication apparatus via the antenna 25. For supplying the NFC transponder 24 and the capacitance measuring device 23 with energy, usually energy is drawn from the field of the external data communication apparatus by the NFC transponder 24 via the antenna 25 and is buffer-stored by the NFC transponder 24 or by the capacitance measuring device 23 in an energy buffer store provided therefor. In this case, the amount of energy that is drawn from the field surrounding the antenna 25 and is buffer-stored in the energy buffer store is sufficient to enable the measurement process that is to be carried out in each case to be concluded.

Furthermore, the arrangement 2 comprises a shield 26 lying on the side opposite the first side, that is to say on the opposite side of the carrier layer relative to the electrodes. In the present exemplary embodiment, the shield is connected to the system ground of the capacitance measuring device 23. However, there are also other possibilities; by way of example, the shield can also be connected to the active potential or, with a correspondingly larger embodiment, it can also be left in a state in which it is not contacted at all.

Alternatively, it is possible for the shield not to be continuous, but rather to lie exactly above the contour of the electrodes. This results in two different shields separated from one another.

Furthermore, this embodiment of the invention also comprises an insulation layer 28, which is arranged on that side of the carrier layer which is opposite the shield 26 or bears against the electrodes 22a, 22b or bears on the latter. The insulation layer 28 is embodied in an adhesive fashion on the side facing away from the electrodes 22a, 22b. As is furthermore evident from FIG. 1, the insulation layer 28 consists of three sublayers, namely a central film 282 and also a first adhesive layer 281, which lies between the film and the electrodes 22a, 22b, and a second adhesive layer 283, which faces the object 1, in particular the human skin to be examined. In addition, there are also numerous other possibilities for producing an insulation layer, for instance as a laminate composite.

FIG. 2 schematically illustrates the capacitance measurement between the two electrodes 22a, 22b. An alternating electric field having a frequency of approximately 100 kHz in the present exemplary embodiment of the invention is applied between the two electrodes 22a, 22b. In principle, frequencies of approximately 40 kHz to approximately 500 kHz can be used for measuring the skin conductivity.

One possibility for capacitance measurement can be implemented by the integrated capacitance measuring device 23 carrying out a sigma-delta method in which the unknown capacitor is pulsed with a fixed voltage. The number of pulses necessary to achieve a fixed reference allows conclusions to be drawn about the capacitance.

In the intermediate region between the two electrodes 22a, 22b, a capacitance forms which can be regarded as parasitic for the present measurement and which is not influenced by the actual measurement variable, namely the moisture of the object, in particular skin, in the topmost region of the object 1. The electric field emanating from the two electrodes 22a, 22b penetrates through the insulation layer 28 into the object 1 or into the upper regions thereof. As a result, the capacitance measured between the two electrodes becomes dependent on the water content in the respective upper layers of skin. In order to prevent the measurement from being influenced by the carrier layer or the adhesive layer, materials having a low relative permittivity of less than 20, in particular of less than 5, are used as materials for the carrier layer 21 and the insulation layer 28. Typical materials for the carrier layer are, for instance, plastics, such as PET or polyimide, or polyester films; typical materials for adhesives would be e.g. acrylate polymers.

The carrier layer 21, the insulation layer 28 and the covering layer 27 are embodied, in principle, as flexible and flat layers in order to enable adaptation to non-planar surfaces.

In order to protect the electronic components used on the carrier layer 21, a covering layer 27 is arranged on the side of the carrier layer 21 on which the shield 26 is situated, said covering layer covering all of the electronic components, in particular the shield. The covering layer 27 is embodied in an electrically insulating fashion and insulates the shield 26 from accesses from outside; this also ensures basic protection, including mechanical basic protection. In the alternative embodiment in FIG. 4, alongside the shield 26, the chip comprising the NFC transponder 24 and the capacitance measuring device 23 and the antenna 25 are also arranged on the opposite side of the carrier layer 21 relative to the electrodes 22a, 22b. These components, too, as illustrated in FIG. 4, are protected from accesses from outside by the covering layer 27.

Figure 4:
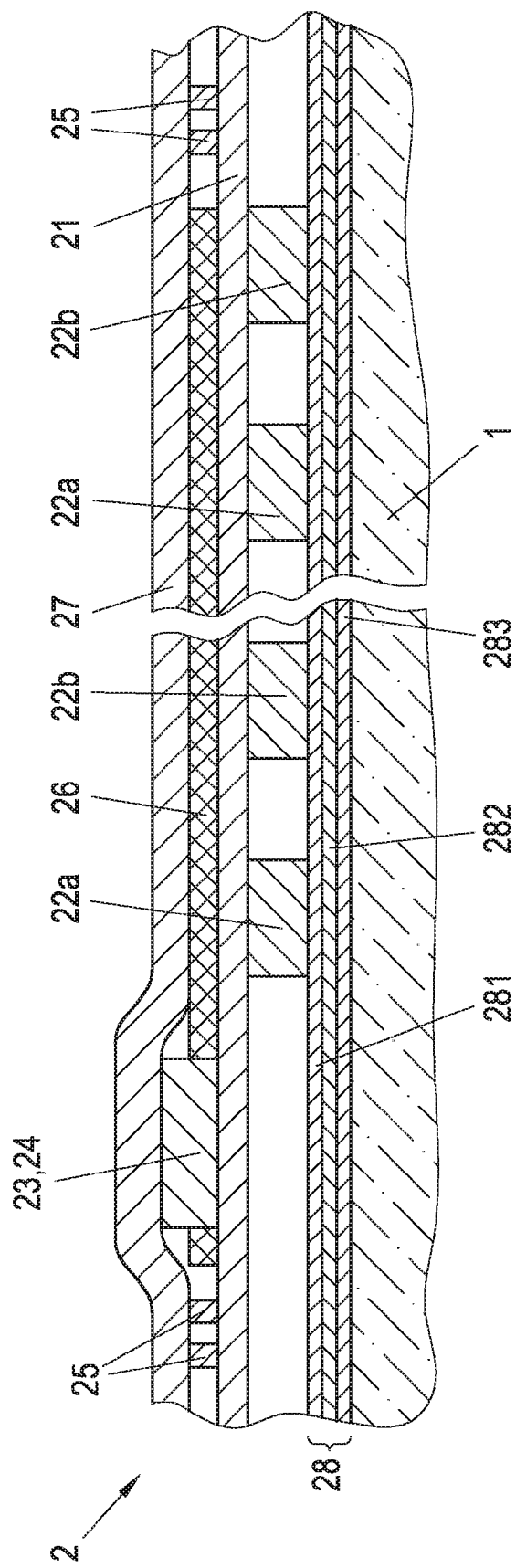
FIG. 4 shows an alternative embodiment of an arrangement according to the invention, in which the capacitance measuring device and the NFC transponder are arranged on the opposite side of the carrier layer relative to the electrodes.

Both in the embodiment illustrated in FIG. 1 and in the embodiment illustrated in FIG. 4, the antenna is embodied as a conductive layer which is applied or arranged completely on one side of the carrier layer 21. In the embodiment of the invention as illustrated in FIG. 1, the antenna is arranged as a layer on the same side as the electrodes 22a, 22b. In particular, the electrodes and also the antenna 25 can be arranged as a printed circuit on the carrier layer 21. As evident from FIG. 3, the antenna in the embodiment illustrated in FIG. 1 is led in a crossover region between the points 251, 252 on the side of the carrier layer facing away from the electrodes.

In all embodiments of the invention it is possible for a battery (not illustrated in the figures) also to be provided instead of or in addition to drawing the energy from the electromagnetic field by means of the antenna, the capacitance measuring device 23 and, if appropriate, also the NFC transponder 24 being connected to said battery. In this case, there is the possibility that the capacitance measuring device 23 measures the capacitance between the electrodes 22a, 22b at automatically predefined points in time and stores said capacitance in a data buffer memory, which can likewise be integrated in the chip jointly with the NFC transponder 24 and the capacitance measuring device 23. Upon request by an external data communication apparatus, there is the possibility that all capacitance measurement values stored in the data buffer memory are transmitted to the external data communication apparatus by the NFC transponder 24.

The two embodiments of the invention that are illustrated below are suitable for suppressing or minimizing the influences of non-constant contact pressure on the measurement results.

Figure 5:
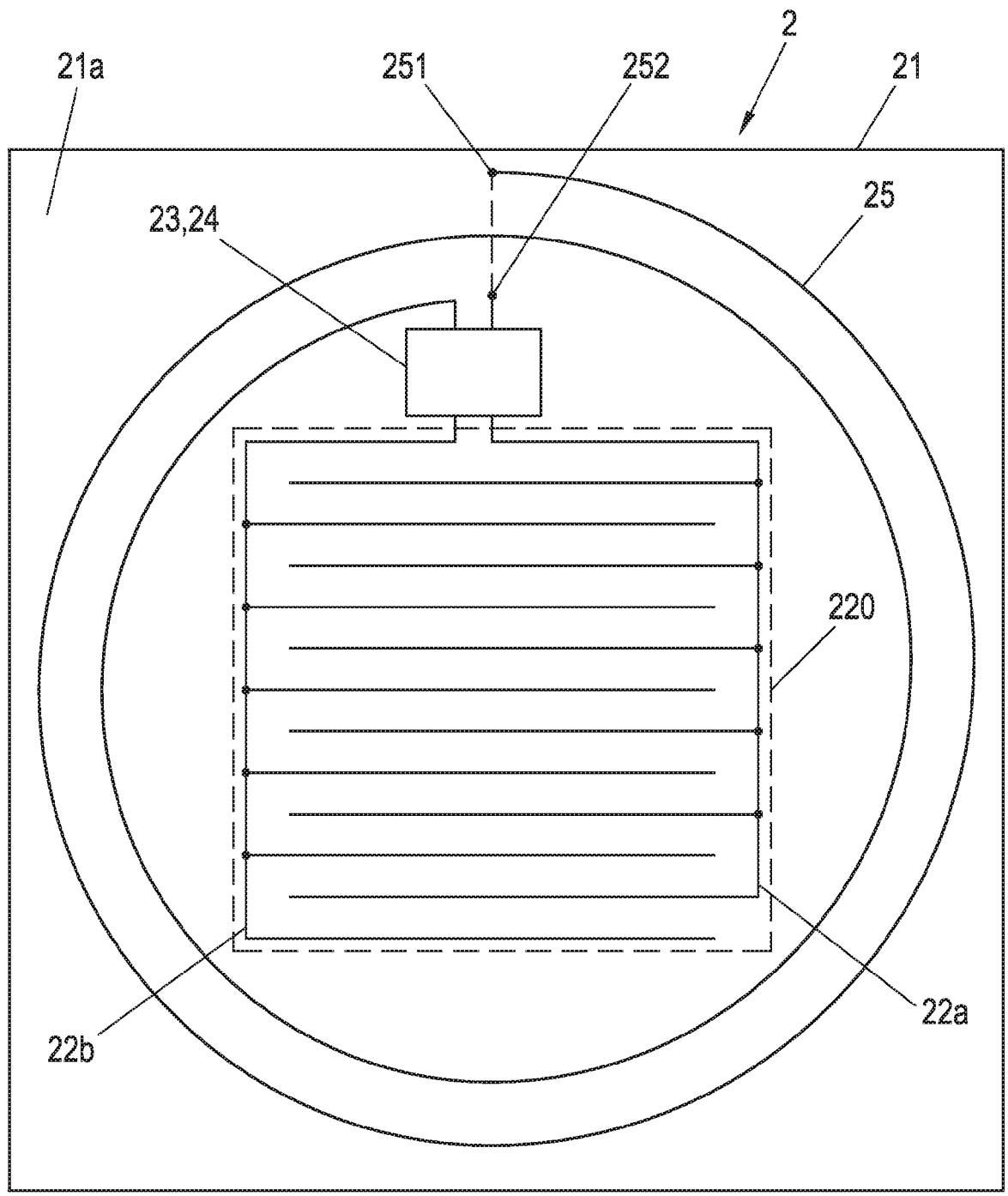
FIG. 5 shows an alternative embodiment of the invention with an edge provided in the carrier.

FIG. 5 illustrates a further preferred embodiment of the invention, which corresponds to the embodiment of the invention illustrated in FIG. 1 or FIG. 4 apart from the details illustrated below. In this embodiment of an arrangement according to the invention, an edge 21a is provided on all sides of the carrier layer 21, said edge being free of electrodes 22a, 22b. In this case, the width of the edge 21a of the carrier layer 21 is at least 15%, in particular at least 30%, of the longest dimension of the area region 220 occupied by the electrodes 22a, 22b. If the area region 220 carrying the electrodes 22a, 22b, is embodied in a rectangular fashion, as in the exemplary embodiment illustrated in FIG. 5, then the carrier layer 21 can likewise be embodied in a rectangular fashion, a circumferential edge 21a being provided. In the embodiment illustrated, the width of the edge 21a corresponds to 50% of the respective edge length of the rectangular area region 220. In order to achieve significant improvements in the measurement, occasionally an edge 21a having a width of at least 15% of the respective edge length of the rectangular area region 220 is also sufficient.

Figure 6:
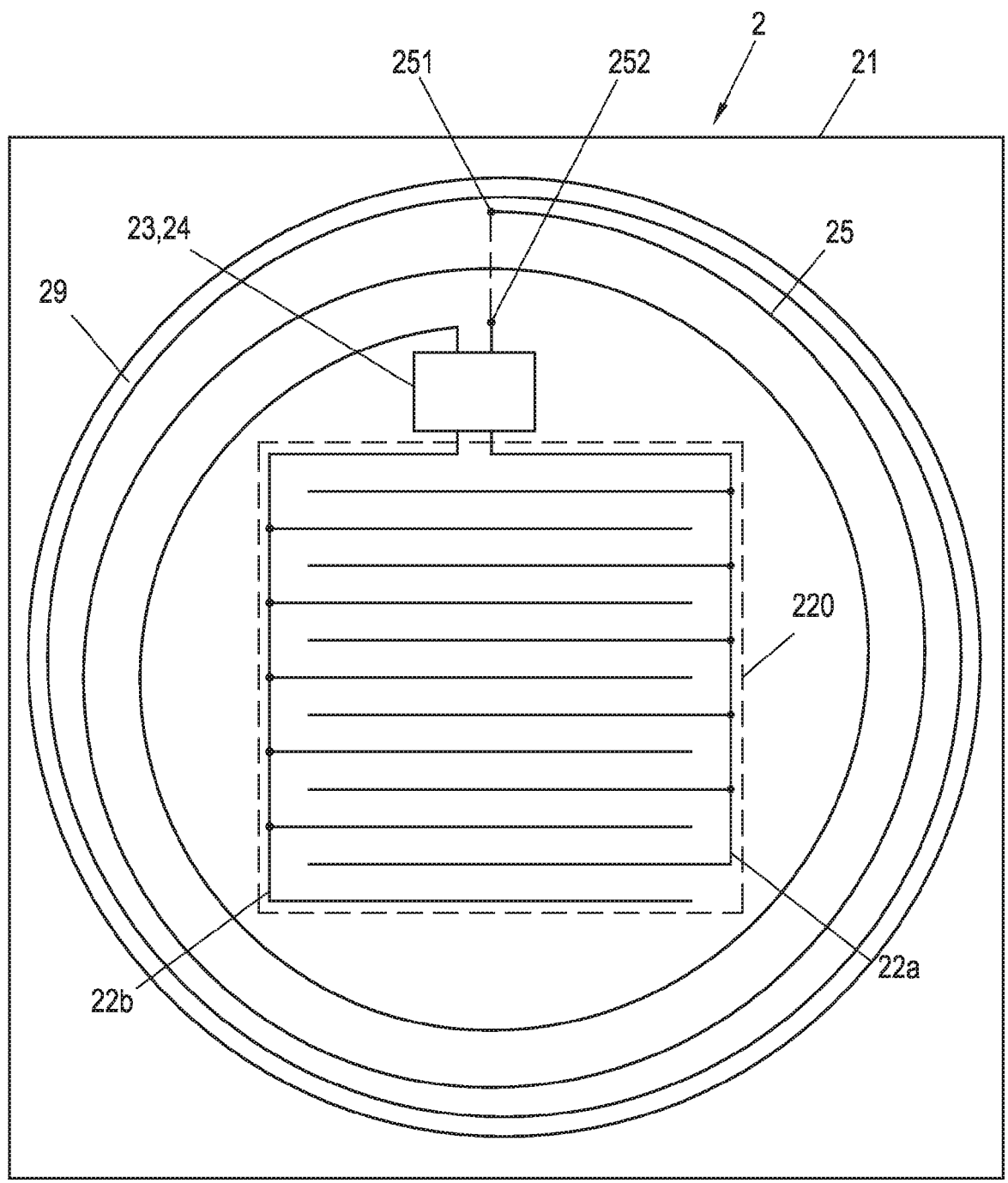
FIGS. 6 and 7 show an alternative embodiment of the invention with a load relieving element arranged on the carrier.
Figure 7:
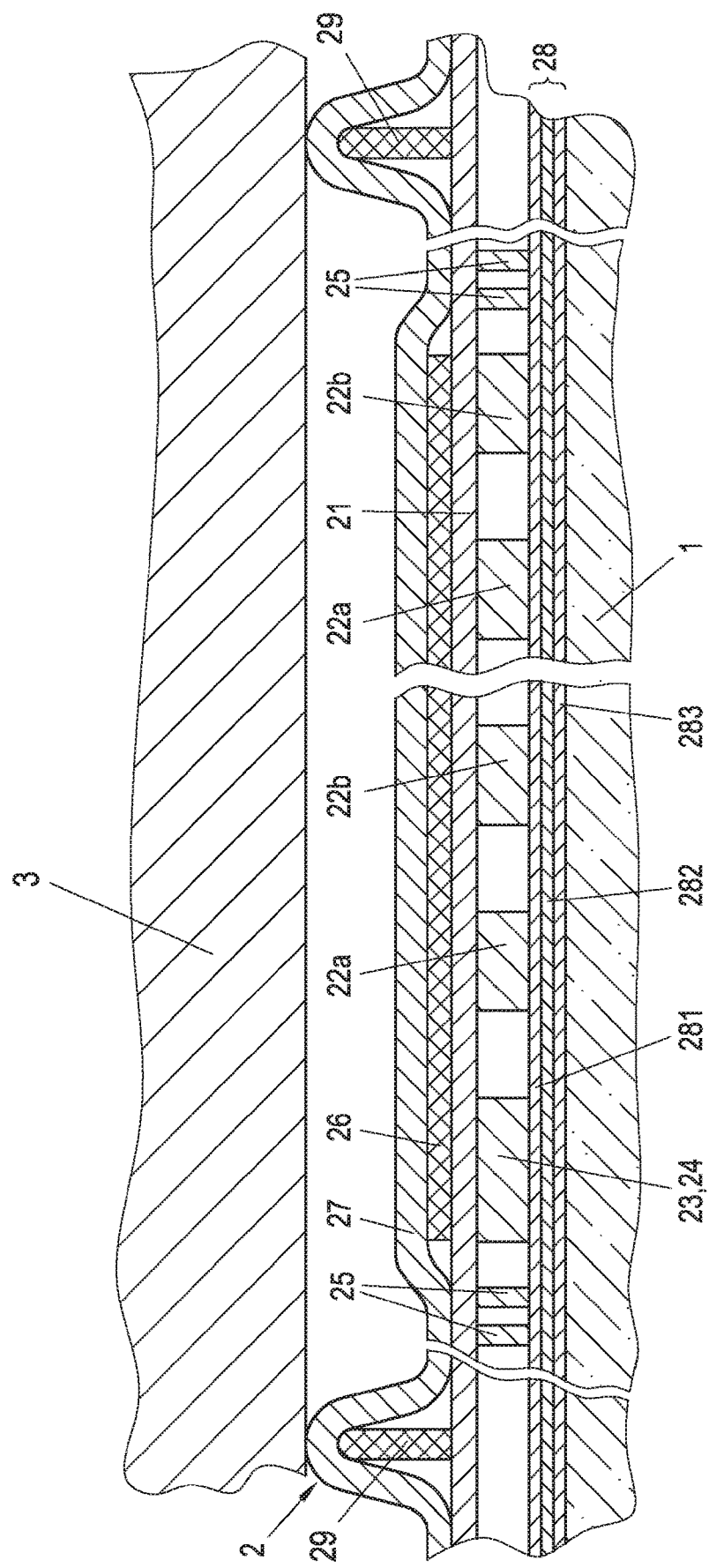

FIGS. 6 and 7 illustrate a further preferred embodiment of an arrangement according to the invention, which corresponds to the embodiment of the invention illustrated in FIGS. 1 and 4 apart from the details illustrated below.

A load relieving element 29 is situated on that side of the carrier 21 which faces away from the object 1 or which is opposite the electrodes 22a, 22b, said load relieving element being embodied as a load relieving ring 29 in the present embodiment. The load relieving element 29 surrounds the electrodes 22a, 22b in such a way that in the event of a flat object 3, such as in particular a reader 3, in particular in the form of a cellular phone 3, bearing on the load relieving element 29, bearing forces do not act on the electrodes 22a, 22b and thus do not distort the measurement result. The load relieving element 29 keeps the reader 3 at a sufficient distance from the electrodes 22a, 22b of the carrier 21. The forces introduced by the reader 3 also act on the carrier at a sufficient distance from the electrodes 22a, 22b to avoid distortions of the carrier 21 in the region of said electrodes 22a, 22b and to relieve the load resulting from stresses and distortions on the carrier 21 in the region of the electrodes 22a, 22b.

The geometry of the load relieving element 29 makes it possible, as illustrated in FIG. 7, to divert the bearing forces into the object 1 or the human body past the electrodes 22a, 22b. In order to ensure this, various embodiments of a load relieving element 29 can be chosen, in principle. In one preferred variant, the load relieving element 29 is formed from flexible rubber material.

The load relieving element 29 is advantageously between 0.5 mm and 2 mm thick. This has the advantage that the load relieving element 29 having this thickness is still easily integrable into the carrier 21 and, on the other hand, keeps the reader 3 sufficiently at a distance to avoid distortions of the carrier in the region of the electrodes 22a, 22b and to relieve the load on the carrier 21 in the region of the electrodes 22a, 22b.

The load relieving element 29 is advantageously arranged within an edge region 21a around the electrodes 22a, 22b which has a width greater than 15% of the longest dimension of the area region 220 occupied by the electrodes 22a, 22b. This distance prevents forces that are exerted via the reader or otherwise from being transmitted into the region of the electrodes 22a, 22b and corrupting the measurement in this way.

In the present application example, said width is between 15% of the longest dimension of the area region 220 occupied by the electrodes 22a, 22b and 200 mm. Said width is between 15% and 200% of the longest dimension of the area region 220 occupied by the electrodes 22a, 22b.

The load relieving element can be positioned both below the covering layer 27 and above the covering layer 27.

In all embodiments, the carrier layer 21 and/or the insulation layer 28 can be embodied in a breathable fashion in order to avoid accumulations of perspiration and liquid.

The invention claimed is:

1. An arrangement for determining the moisture of an object, comprising:
   an insulating layer having a contact face for contacting the object in which the moisture is to be determined;
   at least two interdigital electrodes disposed on and bearing against said insulating layer on a side opposite said contact face;
   an electrically insulating carrier layer disposed on said electrodes on a side of said electrodes opposite said insulating layer;
   a digital capacitance measuring device connected to said electrodes;

an NFC transponder having an antenna, said NFC transponder and said capacitance measuring device are arranged on a common chip, said NFC transponder being configured to receive measurement results of said capacitance measuring device and to forward the measurement results by way of radio via said antenna; and a shield disposed on a side of said carrier layer opposite said electrodes and connected to system ground of said capacitance measuring device.

2. The arrangement according to claim 1, wherein said insulation layer is adhesively connected to a side of said carrier layer.

3. The arrangement according to claim 2, wherein said insulation layer comprises a film, and wherein a first connection layer is disposed on a side of said insulation facing said electrodes, said first connection layer connecting said film to said electrodes and/or to said carrier layer, and which further comprises a second adhesive layer for adhering to the object on a side of said film facing away from said electrodes.

4. The arrangement according to claim 3, wherein said first connection layer is an adhesive layer adhesively connecting said film to said electrodes and/or to said carrier layer.

5. The arrangement according to claim 2, wherein said carrier layer and said insulation layer has a relative permittivity of less than 20.

6. The arrangement according to claim 5, wherein said carrier layer and said insulation layer has a relative permittivity of less than 5.

7. The arrangement according to claim 2, wherein at least one of said carrier layer and said insulation layer is a flexible layer.

8. The arrangement according to claim 1, which comprises a covering layer arranged on a side of said carrier layer on which said shield is disposed.

9. The arrangement according to claim 8, wherein said covering layer is an electrically insulating layer configured to electrically insulate said shield from external access.

10. The arrangement according to claim 8, wherein said covering layer is a flexible layer.

11. The arrangement according to claim 1, wherein said antenna is formed of turns applied and arranged as a conductive layer on a side of said carrier layer.

12. The arrangement according to claim 1, which comprises a battery connected to said capacitance measuring device, and wherein said capacitance measuring device is configured to measure a capacitance between said electrodes at predefined points in time and to store the capacitance in a data buffer memory, and wherein said NFC transponder is configured to transmit all capacitance measurement values in the data buffer memory upon request.

13. The arrangement according to claim 1, wherein said NFC transponder is configured to supply said capacitance measuring device with energy stored in an energy buffer store, which energy was drawn from an electromagnetic field surrounding said antenna.

14. The arrangement according to claim 1, wherein said carrier layer has an edge region that is free of electrodes, wherein a width of said edge region of said carrier amounts to at least 15% of a longest dimension of an area region occupied by said electrodes.

15. The arrangement according to claim 14, wherein the width of said edge region amounts to at least 30% of the longest dimension.

16. The arrangement according to claim 14, wherein said edge region is formed on said carrier layer on all sides.

17. The arrangement according to claim 1, configured for determining a moisture content of human skin.

18. An arrangement for determining the moisture of an object, comprising:
    an insulating layer having a contact face for contacting the object in which the moisture is to be determined;
    at least two electrodes disposed on and bearing against said insulating layer on a side opposite said contact face;
    an electrically insulating carrier layer disposed on said electrodes on a side of said electrodes opposite said insulating layer;
    a digital capacitance measuring device connected to said electrodes;
    an NFC transponder having an antenna, said NFC transponder being configured to receive measurement results of said capacitance measuring device and to forward the measurement results by way of radio via said antenna; and a shield disposed on a side of said carrier layer opposite said electrodes and connected to system ground of said capacitance measuring device;
    a load relieving element disposed on the side of said carrier layer opposite said electrodes, said load relieving element projecting from said carrier layer and being arranged within an edge region around said electrodes, said edge region having a width greater than 15% of a longest dimension of an area region encompassed by said electrodes.

19. The arrangement according to claim 18, wherein said load relieving element has a thickness of between 0.5 mm and 2 mm.

* * * * *